United States Patent
England et al.

(10) Patent No.: US 11,635,519 B2
(45) Date of Patent: *Apr. 25, 2023

(54) ONSCENE COMMAND VISION

(71) Applicant: Intergraph Corporation, Madison, AL (US)

(72) Inventors: Andrew James England, Harvest, AL (US); Laura Beth Ezzell, Vestavia Hills, AL (US); Thomas Overfield, Huntsville, AL (US); Renz Angelo Santos, Huntsville, AL (US); Edward Michael Sieja, Madison, AL (US); Charles Carlton Barnes, Huntsville, AL (US)

(73) Assignee: Intergraph Corporation, Madison, AL (US)

( * ) Notice: Subject to any disclaimer, the term of this patent is extended or adjusted under 35 U.S.C. 154(b) by 463 days.

This patent is subject to a terminal disclaimer.

(21) Appl. No.: 16/846,093

(22) Filed: Apr. 10, 2020

(65) Prior Publication Data

US 2020/0241142 A1 Jul. 30, 2020

Related U.S. Application Data

(63) Continuation of application No. 16/006,052, filed on Jun. 12, 2018, now Pat. No. 10,656,274.

(60) Provisional application No. 62/518,167, filed on Jun. 12, 2017.

(51) Int. Cl.
*G01S 17/48* (2006.01)
*G01S 17/89* (2020.01)
*A61B 5/00* (2006.01)
*A61B 5/08* (2006.01)
*G06T 17/20* (2006.01)
*G06Q 10/06* (2023.01)
(Continued)

(52) U.S. Cl.
CPC .............. *G01S 17/48* (2013.01); *A61B 5/002* (2013.01); *A61B 5/0008* (2013.01); *A61B 5/08* (2013.01); *G06Q 10/06* (2013.01); *G06Q 10/08* (2013.01); *G06Q 50/28* (2013.01); *G06T 17/20* (2013.01)

(58) Field of Classification Search
CPC ........ G01S 17/48; G06Q 50/28; G06Q 10/08; G06Q 10/06; A61B 5/0008; A61B 5/002; A61B 5/08; G06T 17/20
USPC ........................................................ 356/3.01
See application file for complete search history.

(56) References Cited

U.S. PATENT DOCUMENTS 5,952,922 A 9/1999 Shober
6,307,475 B1 10/2001 Kelley
(Continued)

OTHER PUBLICATIONS

Bahl, P., et al., "RADAR: An In-Building RF-Based User Location and Tracking System," Proceedings IEEE INFOCOM 2000, pp. 775-784 (Mar. 26-30, 2000).
(Continued)

*Primary Examiner* — Daniel L Murphy
(74) *Attorney, Agent, or Firm* — Nutter McClennen & Fish LLP

(57) ABSTRACT

Embodiments use holographic projection in augmented reality to visualize a building in 3D and show, as a holographic figure, the position of personnel in the building. In some embodiments, a user can "tap" on a holographic figure to view data on that person, such as skin temperature, room temperature, heart rate, etc.

31 Claims, 14 Drawing Sheets

(51) Int. Cl.
    *G06Q 10/08*    (2023.01)
    *G06Q 50/28*    (2012.01)

(56) References Cited

U.S. PATENT DOCUMENTS

| | | | |
|---|---|---|---|
| 8,471,706 B2 * | 6/2013 | Schuster | G06Q 10/08 340/572.1 |
| 8,773,946 B2 | 7/2014 | Padmanabhan et al. | |
| 8,798,924 B2 | 8/2014 | Haverinen | |
| 8,884,742 B2 | 11/2014 | Gits et al. | |
| 8,896,595 B2 | 11/2014 | Boersma et al. | |
| 9,078,104 B2 | 7/2015 | Haverinen | |
| 9,080,874 B2 | 7/2015 | Haverinen | |
| 9,151,621 B2 | 10/2015 | Haverinen | |
| 9,154,914 B2 | 10/2015 | Haverinen | |
| 9,253,601 B2 | 2/2016 | Haverinen | |
| 9,316,501 B2 | 4/2016 | Haverinen | |
| 9,476,717 B2 | 10/2016 | Haverinen et al. | |
| 9,521,522 B2 | 12/2016 | Haverinen | |
| 9,544,730 B2 | 1/2017 | Haverinen | |
| 9,599,473 B2 | 3/2017 | Haverinen | |
| 9,674,672 B1 | 6/2017 | Haverinen et al. | |
| 9,683,851 B2 | 6/2017 | Haverinen | |
| 9,933,508 B2 | 4/2018 | Haverinen et al. | |
| 10,656,274 B2 * | 5/2020 | England | G06Q 50/28 |
| 2007/0120671 A1 | 5/2007 | Carmichael et al. | |
| 2013/0177208 A1 | 7/2013 | Haverinen | |
| 2013/0179074 A1 | 7/2013 | Haverinen | |
| 2013/0179075 A1 | 7/2013 | Haverinen | |
| 2013/0310069 A1 | 11/2013 | Haverinen | |
| 2014/0286534 A1 | 9/2014 | Haverinen | |
| 2014/0357305 A1 | 12/2014 | Haverinen et al. | |
| 2015/0260524 A1 | 9/2015 | Haverinen | |
| 2016/0135012 A1 | 5/2016 | Haverinen | |
| 2016/0202064 A1 | 7/2016 | Haverinen | |
| 2016/0300389 A1 | 10/2016 | Glenn, III et al. | |
| 2016/0350811 A1 | 12/2016 | Perttunen et al. | |
| 2017/0180948 A1 | 6/2017 | Haverinen et al. | |
| 2018/0132555 A1 | 5/2018 | Gonzalez | |
| 2018/0356523 A1 | 12/2018 | England et al. | |

OTHER PUBLICATIONS

Kumar et al., "Robot and Sensor Networks for First Responders," Pervasive Computing, pp. 24-33, IEEE (2004).

Woodman, O. et al., "Pedestrian Localisation for Indoor Environments," Proceedings of the 10th International Conference on Ubiquitous Computing—UbiComp '08, pp. 114-123 (Sep. 21-24, 2008).

Parnandi, A., et al., "Coarse In-Building Localization with Smartphones," Lecture Notes of the Institute for Computer Sciences, Social Informatics and Telecommunications Engineering, vol. 35, 12 pages (Oct. 25, 2009).

Matsumoto, "Real-Time Multi-Sensor Localisation and Mapping Algorithms for Mobile Robots," Flindeers University Ph.D. thesis, 309 pages (2009).

International Search Report and Written Opinion for Application No. PCT/US2018/03706, dated Sep. 18, 2018, 12 pages.

European Patent Office, Office Action—Communication Pursuant to Artciel 94(3) EPC for Application No. 18/739,978, dated Mar. 2, 2021, 6 pages.

European Patent Office, Office Action—Summons to Attend Oral Proceedingsfor Application No. 18739978, dated Jan. 17, 2022, 8 pages.

Chinese Office Action for Application No. 201880038399, dated Feb. 18, 2022, 14 pages.

Chinese Search Report for Application No. 201880038399, dated Feb. 18, 2022, 6 pages.

* cited by examiner

ONSCENE COMMAND VISION

RELATED APPLICATIONS

This patent application claims priority from U.S. non-provisional patent application Ser. No. 16/006,052, filed Jun. 12, 2018, titled "OnScene Command Vision," and naming Andrew James England; Laura Beth Ezzell; Thomas Overfield; Renz Angelo Santos, Edward Michael Sieja, and Charles Carlton Barnes as inventors, and from provisional U.S. patent application No. 62/518,167, filed Jun. 12, 2017, entitled, "OnScene Command Vision," and naming Andrew England; Laura Beth Ezzell; Thomas Overfield; Renz Santos and Ed Sieja as inventors, the disclosures of each of which is incorporated herein, in its entirety, by reference.

TECHNICAL FIELD

The present invention relates to determining the location of persons within a building, and more particularly to remotely monitoring the location of persons within a building.

BACKGROUND ART

It is known in the art to determine the location of a person within a building by, for example, direct personal observation by an observer of such person's location, or through the use of cameras.

It is also know in the art to determine the location of a person within a building by remote sensing technology. Some prior art systems monitor the location of a person, relative to a modality remote from the person, by GPS or other triangulation techniques.

SUMMARY OF THE EMBODIMENTS

In accordance with one embodiment of the invention, a system for identifying the location of an agent within an interior of a building, the system includes a location receiver configured to obtain locator information from the agent, the locator information indicating the location of the agent relative to a reference frame; and a model receiver configured to procure a 3D model of the interior of the building.

The system also includes a correlator configured to correlate the 3D model to the reference frame, to produce a correlated location representing the location of the agent within the building.

The system also includes a rendering module configured to render a 3D image from the 3D model and correlated location, the 3D image including an avatar representing the agent at the correlated location within the 3D image, as well as a 3D display device in communication with the rendering module, the 3D display device configured to receive and display, to a user, the 3D image.

Some embodiments also include a telemetry receiver configured to receive, from a transmitter with the agent, telemetry data. For example, the telemetry data may include the ambient temperature of the agent's location within the interior of the building. In some embodiments, the telemetry data includes biotelemetry data, such as at least one of the skin temperature of the agent; the respiration rate of the agent; and/or the heart rate of the agent. In such embodiments, the correlator is further configured to correlate the biotelemetry data with the correlated location. Moreover, in some such embodiments the rendering module is further configured to render, into the 3D image, a telemetry window at the correlated location so that the telemetry data is visually associated with the agent represented by the avatar.

Some embodiments also include a reference frame module configured to procure a reference frame. In such embodiments, the correlator is further configured to correlate the locator information to the reference frame, and to correlate the reference frame to the building model.

Some embodiments include a locator device disposed with the agent in the building, the locator device having a transmitter configured to transmit the locator information. In some embodiments, the locator device further includes a magnetic sensor in data communication with the transmitter.

Another embodiment includes a method of displaying the location of an agent within an opaque building. The method includes receiving locator information from the agent, the locator information indicating the location of the agent relative to a reference frame.

The method also includes receiving a 3D model of the interior of the building, and correlating the 3D model to the reference frame, to produce a correlated location representing the location of the agent within the building. For example, in some embodiments, the 3D model includes a point cloud, or a surface reconstruction produced from a point cloud.

In some embodiments, correlating the 3D model to the reference frame includes procuring a reference frame; and correlating both the locator information and the building model to the reference frame.

The method further includes rendering a 3D image from the 3D model and correlated location. The 3D image includes an avatar representing the agent at the correlated location within the 3D image. Then, the method displays the 3D image on a 3D display device.

In some embodiments the method includes receiving, from a transmitter with the agent, telemetry data; and correlating the telemetry data with the correlated location. Such embodiments also include rendering into the 3D image a telemetry window at the correlated location so that the telemetry window is visually associated with the agent represented by the avatar. For example, some embodiments render the telemetry window at the correlated location in response to user input received at the displayed avatar.

In some embodiments, the locator information includes a set of magnetic readings from the location of the agent within the building; and the reference frame includes a plurality of magnetic vectors from known locations within the building. In such embodiments, correlating both the locator information and the building model to the reference frame includes determining the correlated location of the agent within the building by matching the set of magnetic readings to a corresponding set of magnetic vectors.

Yet another embodiment includes a system for producing a 3D map of a building's interior. The system includes a mobile contemporaneous capture modality capable of moving throughout the interior of the building, as well as a sensor system disposed on the mobile modality to generate the 3D map as the mobile modality moves throughout the building.

In some embodiments, the mobile modality includes an autonomous conveyor apparatus.

In some embodiments, the sensor system includes a laser scanner that produces, as acquired data, a point cloud of physical measurements representing the interior of the building. In some embodiments the sensor system includes a magnetic sensor that produces, as acquired data, a set of magnetic readings collectively defining a magnetic signature of the interior of the building.

The sensor system in some embodiments includes both a laser scanner that produces, as acquired data, a point cloud of physical measurements representing the interior of the building; and a magnetic sensor that produces, as acquired data, a set of magnetic readings collectively defining a magnetic signature of the interior of the building. In such embodiments, the laser scanner and the magnetic sensor disposed on the mobile modality such that the sensor system produces both the point cloud and the magnetic readings contemporaneously on the same pass of the mobile modality through the building.

In some embodiments, the system also includes a mapping module configured to correlate (i) a point cloud of physical measurements of the interior of the building gathered by the sensor system with (ii) a magnetic signature of the interior of the building gathered by the sensor system, to produce a hybrid 3D map of the interior of the building.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

Figure 1A:
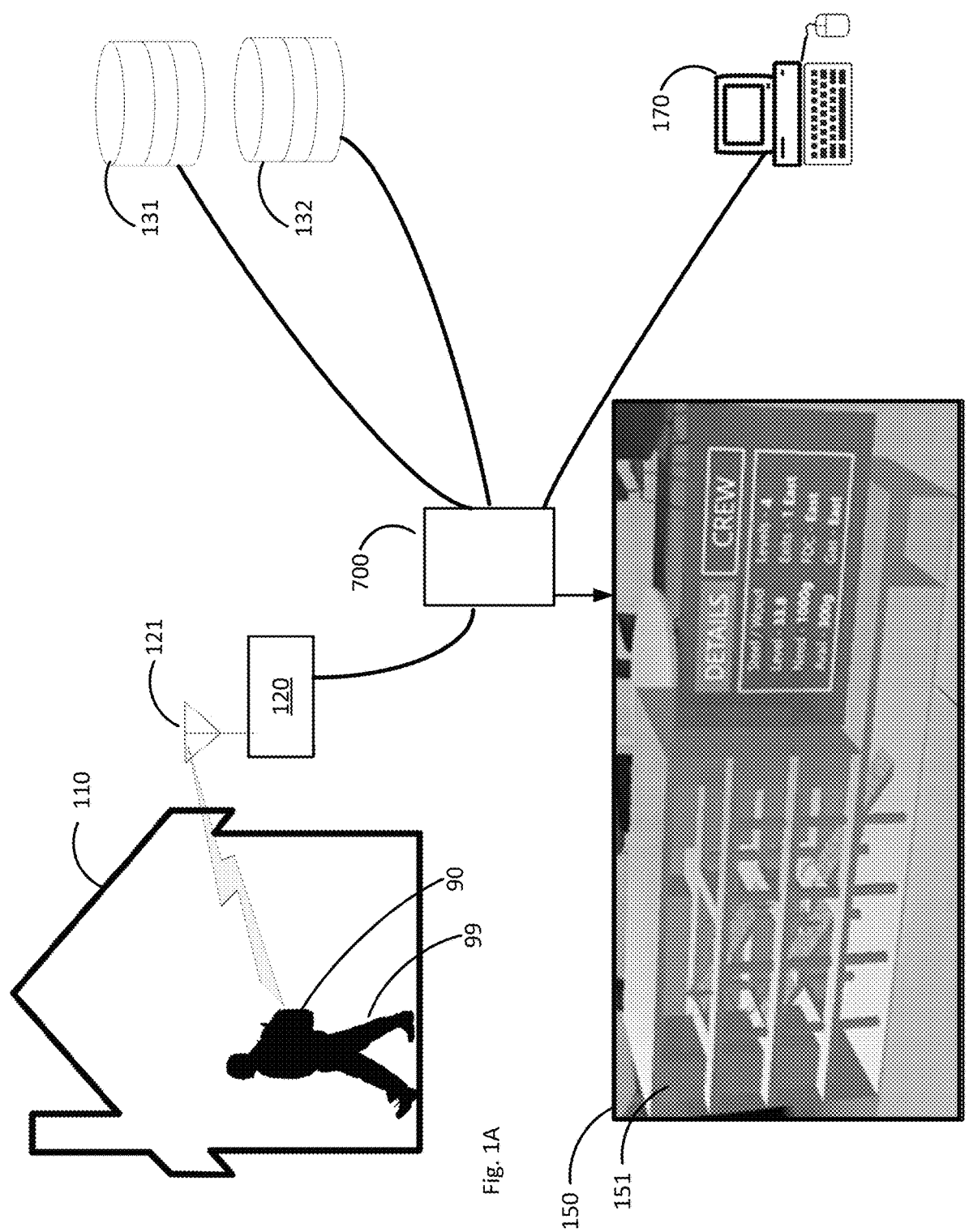
FIG. 1A schematically illustrates and environment for various embodiments.

Various embodiments enable a display device to show, to a person outside of an opaque building, the location of another person inside of that opaque building. For convenience, illustrative embodiments refer to the person inside the building as an agent 99, and the person outside the building as a manager 188, although that terminology does not imply an agency or managerial relationship between them.

Illustrative embodiments display the location of an agent 99 within a 3D rendering of a building 110 using a 3D model 310 of the building 110 in conjunction with locator information that identifies the location of the agent 99. The location information is correlated to the 3D model 310 so that an avatar 299 of the user 99 can be graphically disposed within the 3D rendering of the building. Some embodiments correlate the locator information to the 3D model 310 by correlating both to a third dataset, such as a magnetic map.

Moreover, in some embodiments, the manager 188 is able to cause the display of biometric data 261 of the agent 99 in a biometric display 260. For example, the manager 188 may cause the display of the biometric data 261 by selecting the avatar 299. An avatar 299 may be selected in a variety of ways, such as by clicking on the avatar 299 with a mouse or other controller, or by hand gestures as known in the art of virtual reality headsets such as Oculus Rift or HTC Vive. In some embodiments, the biometric display 260 is displayed near the avatar 299 of the agent 99 to which the biometric data 261 applies so as to correlate the biometric data 261 to that agent. This is beneficial, for example, when two or more avatars 299 are shown, so that a user can determine which avatar 299 is associated with which biometric display 260.

It should be noted that preferred embodiments are capable of determining the location of the agent 99, all without requiring sensors within the building 110 to identify the location of the agent 99.

FIG. 1A schematically illustrates an illustrative environment for use of a system that allows a manager 188 to know and track the position of an agent 99 inside of a building 110. In illustrative embodiments, the building 110 may be experiencing an emergency, the agent 99 may be a responder (e.g., fireman; police; paramedic), and the manager 188 may be an on-scene commander.

Figure 6:
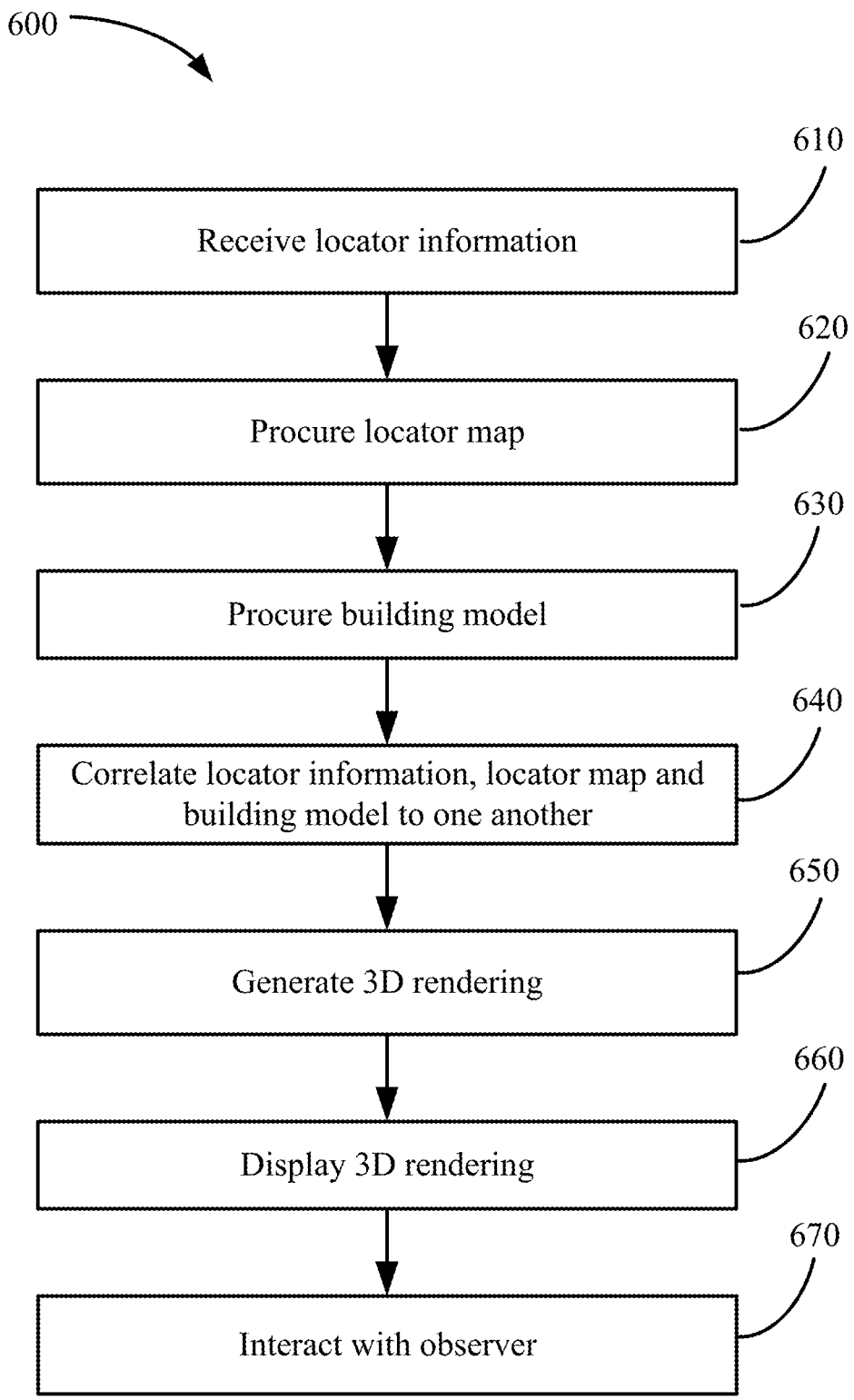
FIG. 6 is a flow chart of a method for displaying the location of a person within a building on a 3D rendering of that building.

Illustrative embodiments may be understood by reference to the method 600, schematically illustrated in a flow chart in FIG. 6. An overview of that method is described in connection with FIG. 6, and can be further understood from additional description herein.

Overview

Figure 7:
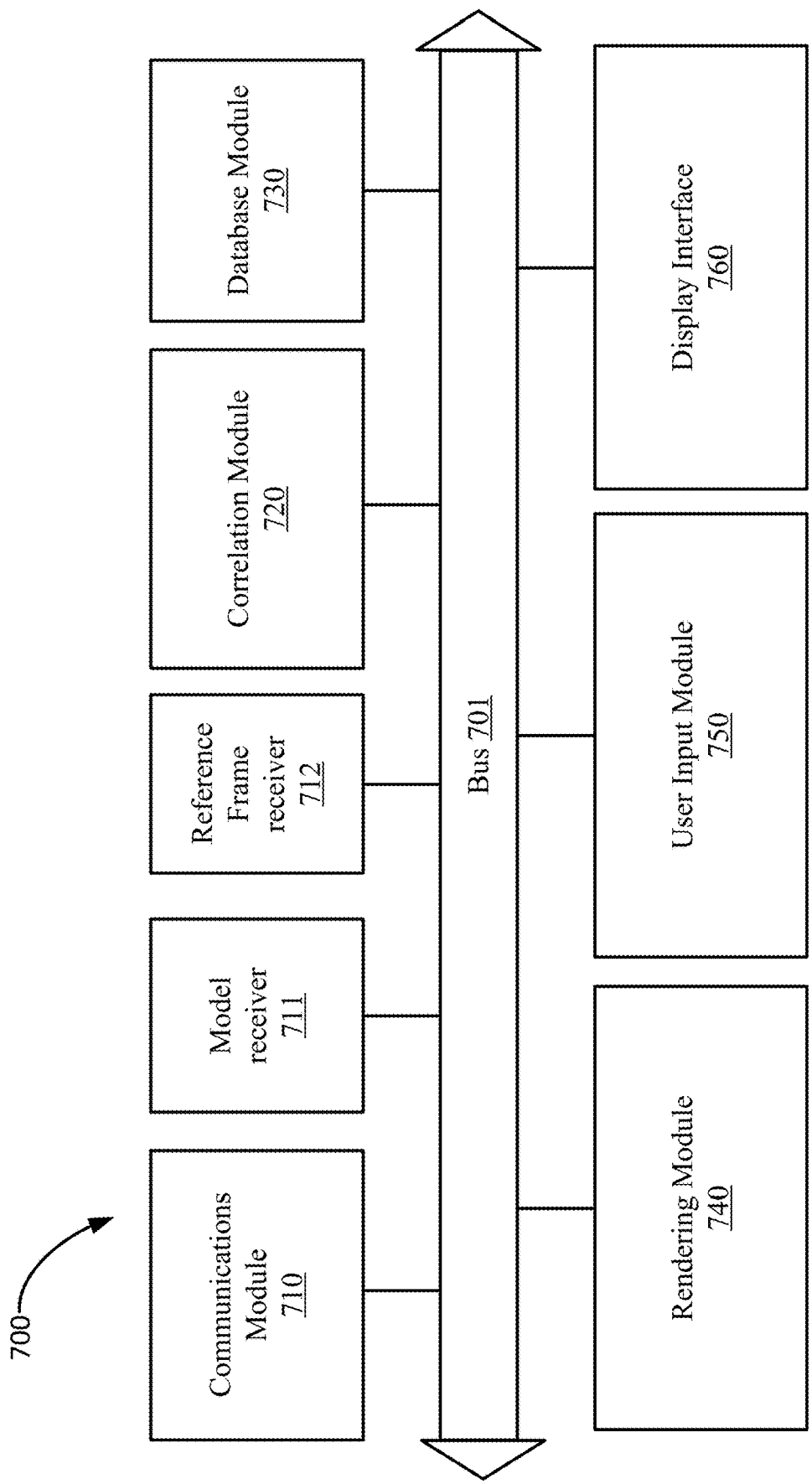
FIG. 7 schematically illustrates a system for displaying the location of a person within a building on a 3D rendering of that building.

In illustrative embodiments, a system (e.g. 700; FIG. 7) receives locator information at step 610. The locator information includes data that can be used to identify the location of the agent 99 relative to a framework. For example, locator information may be provided by a locator device 90, embodiments of which are described below, worn by or carried by the agent 99.

Figure 1B:
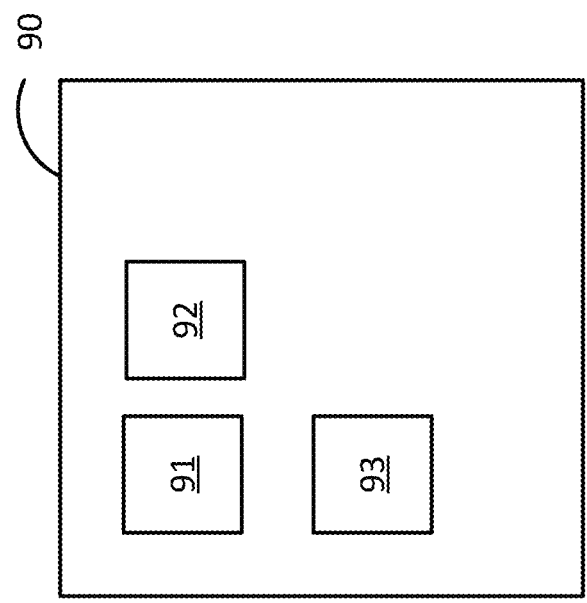
FIG. 1B schematically illustrates an embodiment of a locator device.

An illustrative embodiment of a locator device 90 is schematically illustrated in FIG. 1B, and includes a radio transmitter 91 and a set of sensors 92 (wherein a set includes at least one sensor). In this illustrative embodiment, the set of sensors 92 includes magnetic sensor disposed to measure the Earth's magnetic field at the location of the agent 99. In general, the set of sensors 92 may include other sensors, such a heart rate sensor disposed to measure the heart rate of agent 99, a respiration sensor disposed to measure the respiration rate of agent 99, a skin temperature sensor disposed to measure the skin temperature of agent 99, and a thermometer disposed to measure the ambient temperature of the location of agent 99.

It is known that a building 110, or its components (e.g., steel beams) distort the Earth's magnetic field. The magnitude and direction of the Earth's magnetic field varies within the building, for example as a function of the proximity of magnetic-field-distorting building components. Such distortions may be mapped throughout the building to produce a magnetic map. The magnetic map may be stored, such as in a database 131. A measurement, by the sensor 92, of the Earth's magnetic field at any point within the building 110 may be compared to the magnetic map, and the location of the sensor 92 within the building 110 may thereby be determined with a high degree of precision. Consequently, the location within the building 110 of the agent 99 carrying the sensor 92 may likewise be determined with a high degree of precision.

In another embodiment, the transmitter 91 may periodically transmit a ping signal. The ping signal may be received by a plurality of triangulation receivers 406 disposed within or surrounding the building 110. Through a process of triangulation, the location of the transmitter 91 within the building 110 may be accurately determined.

Some embodiments use the transmitter 91 to transmit data measured by sensor 91 (or measurements by the sensor set 92; e.g., the heart rate of agent 99, the respiration rate of agent 99, the skin temperature of agent 99; the ambient temperature of the location of agent 99, to name but a few examples) to the antenna 121 of a receiver 120. The receiver 120 is a part of, or at least is in data communication with, a system 700 to provide the measured data to the system 700.

At step 620, the method 600 procures a reference frame 400, embodiments of which are described below. The reference frame 400 enables correlation of the locator information to a building model 310. In some embodiments, the reference frame 400 is stored in and retrieved from a reference frame database 131.

At step 630, the method 600 procures a building model 310, embodiments of which are described below. The building model 310 includes structural detail of the building 110. In some embodiments, the building model 310 is stored in and retrieved from a building model database 132.

At step 640, the method correlates the locator information, reference frame, and building model to one another.

Step 650 generates a 3D rendering 210 of the building 110, including an avatar 299 of the agent 99 relative to the building 110.

The method 600 then displays, preferably on a 3D display device 150, the 3D rendering, including the avatar 299.

Optionally, at step 670, the method interacts with an observer 188. For example, the observer 188 may activate (e.g., click-on, tap on, or otherwise gesture to) the avatar 299 to cause the display device 150 to show additional information, such as telemetric data relating to the agent 99 or the environment within the building 110 at the location of the agent 99. Some embodiments also allow the observer 188 to manipulate the rendering (e.g., to rotate the 3D rendering; zoom-in; zoom-out, etc.)

Building Model

In illustrative embodiment, a 3D model 310 of a building 110 is stored in a memory, such as a building model database 132, having been created at a prior time. Such a 3D model may be referred to as an "a priori" building model 310.

In preferred embodiments, the 3D model is (or includes or is created from) a point cloud, such as a point cloud produced by a laser scanner from within the building 110. In preferred embodiments, the 3D model is not raw point cloud data, but is instead a model of the interior of the building based on a point cloud. In some embodiments, the 3D model is a surface mesh 3D model. In preferred embodiments, the 3D model is a parametric 3D model. Such 3D models may be created using CAD software as known in the art, such as Autodesk Revit with the Leica CloudWorx plugin available from Leica Geosystems to name but one example.

Figure 3A:
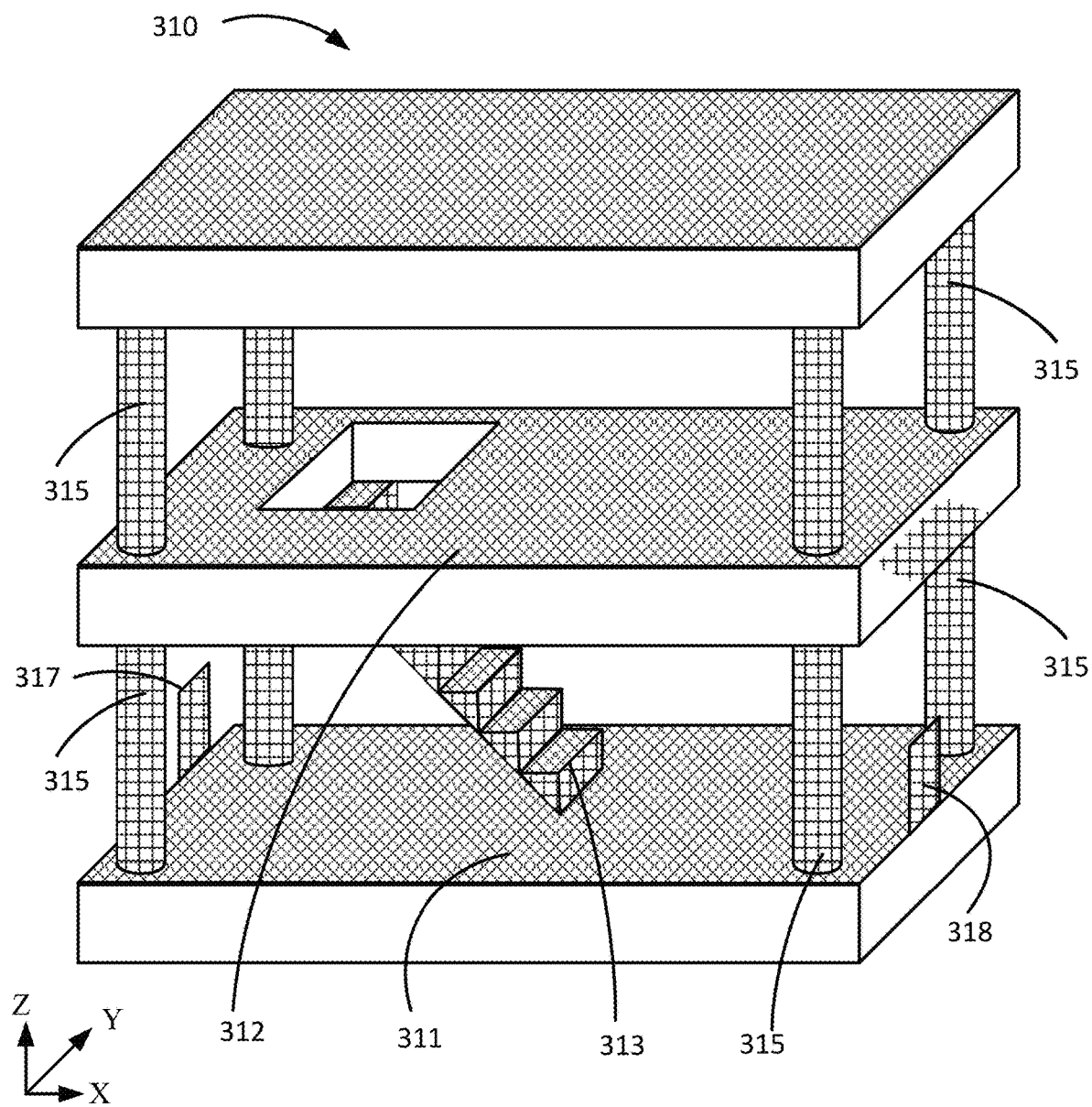
FIG. 3A schematically illustrates an embodiment of point cloud of an interior of a building.

A point cloud 310 of the interior of building 110 is schematically illustrated in FIG. 3A, in which surfaces of the interior of the building 110 are represented by hashing patterns in which each vertex of the hatching pattern represents a point in the point cloud.

Figure 3B:
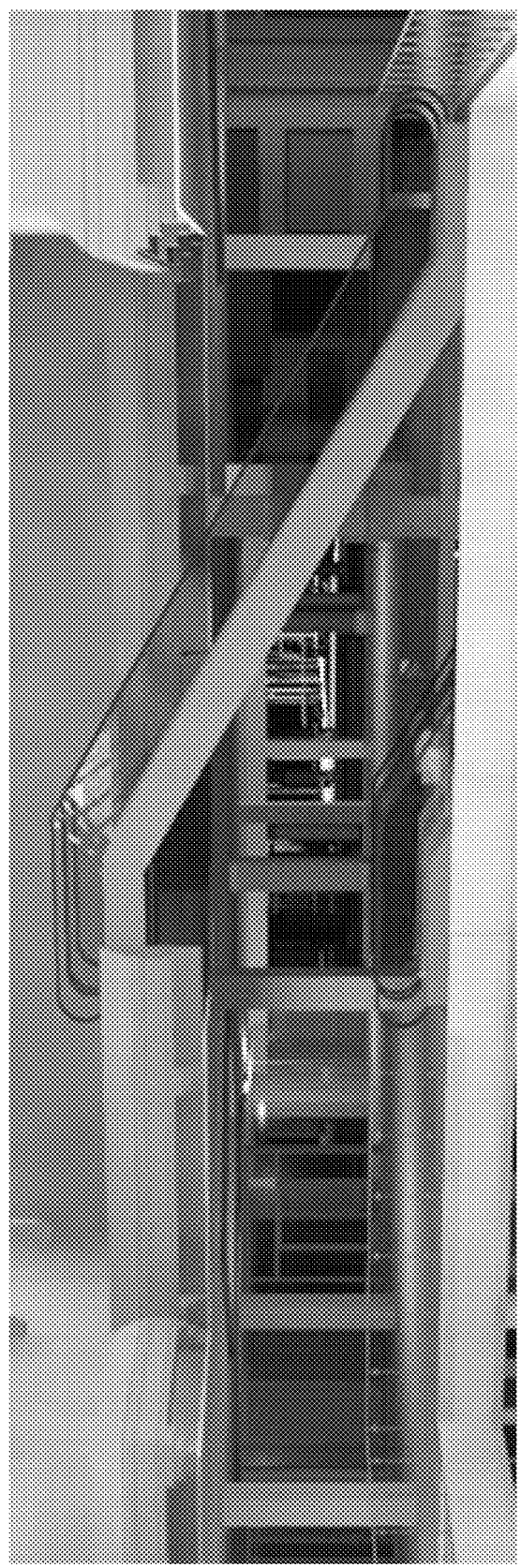
FIG. 3B schematically illustrates an embodiment of a rendering of a building based on a point cloud.

As known in the art of laser scanning, a point cloud produces a dense array of points by measuring the inside of a building 110 with a laser scanner. Each point in the array of points represents a physical point of a surface within the building, and has a known spatial relationship with all other points in the point cloud, so that collectively the points form a detailed representation of the interior of the building 110. In some embodiments, the point cloud records (and when displayed, reveals) details of the interior of the building that are at least photographic quality. For example, the image 311 in FIG. 3B is a 2D rendering of a surface reconstruction of the interior of a building, such as building 110, created from a point cloud obtained by a Leica BLK360 laser scanner available from Leica Geosystems.

A point cloud has advantages over a photograph, however, in that individual points in the array can be manipulated, such as by a computer programmed for that purpose, to yield a 3D rendering of the interior of the building 110. In preferred embodiments, a point cloud, and/or an image developed based on a point cloud, can be manipulated by a user in ways that enable options for viewing the image. Such manipulations may include rotating the image, and/or zooming-in and/or zooming-out of the image, to name but a few examples.

Figure 3C:
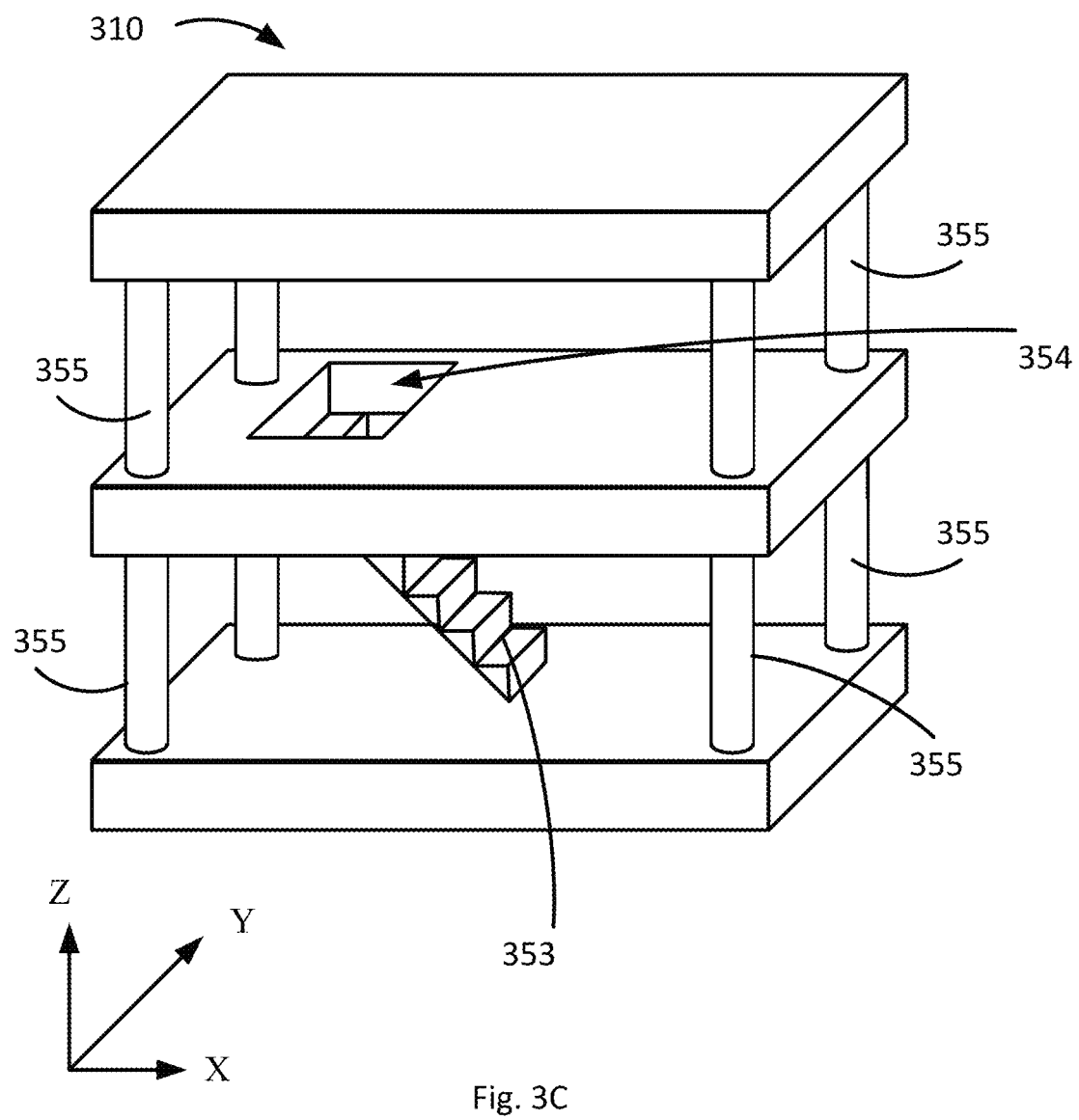
FIG. 3C schematically illustrates an embodiment of a CAD model of the building.

In other embodiments, the 3D model 310 may be a rendering produced by a computer-aided design ("CAD") system, such as the CAD model 350 of building 110 schematically illustrated in FIG. 3C. For example, an architect might create such a CAD model 350 in the process of designing the building 110. Alternatively, such a CAD model 350 may be developed after the building is built by, for example, an artist or surveyor observing the interior of the building 110.

Agent Location {Reference Frame}

Once within the building 110, the agent 99 is typically not visible from outside the building 110. This raises the challenge of how to determine the location of the agent 99, preferably from outside the building, and preferably without the use of building infrastructure.

Illustrative embodiments locate the agent 99, from outside the building 110, with respect to a reference frame.

For example, an illustrative embodiment locates the agent 99 from outside the building 110 through triangulation. To that end, one, two or more triangulation reference transmitters 406 may be disposed around the outside of the building 110. For example, such triangulation reference transmitters 406 may be placed at known structural elements of the building 110, such as a door 117 and one or more corner 119.

In addition, an array of triangulation receivers 405 is disposed around the outside of the building 110. The triangulation receivers 405 receive signals from the triangulation reference transmitters 406, and the system 700 can be said to know the locations of the triangulation reference transmitters 405 with respect to one another, thereby defining a 3D Cartesian reference frame (X, Y, Z axes) relative to the building.

Figure 4A:
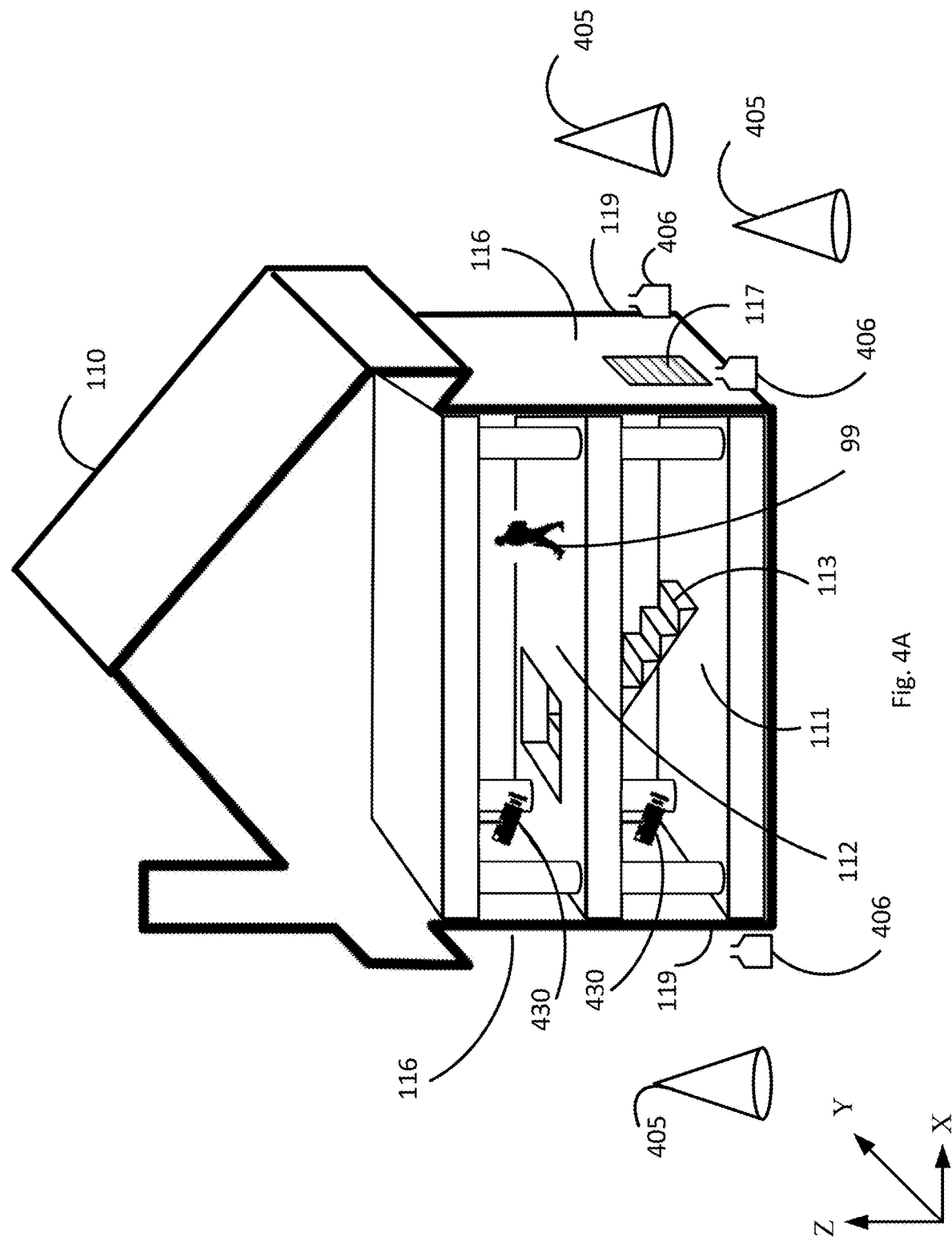
FIG. 4A schematically illustrates an embodiment of a system for determining the location of a person within a building by triangulation.
Figure 4B:
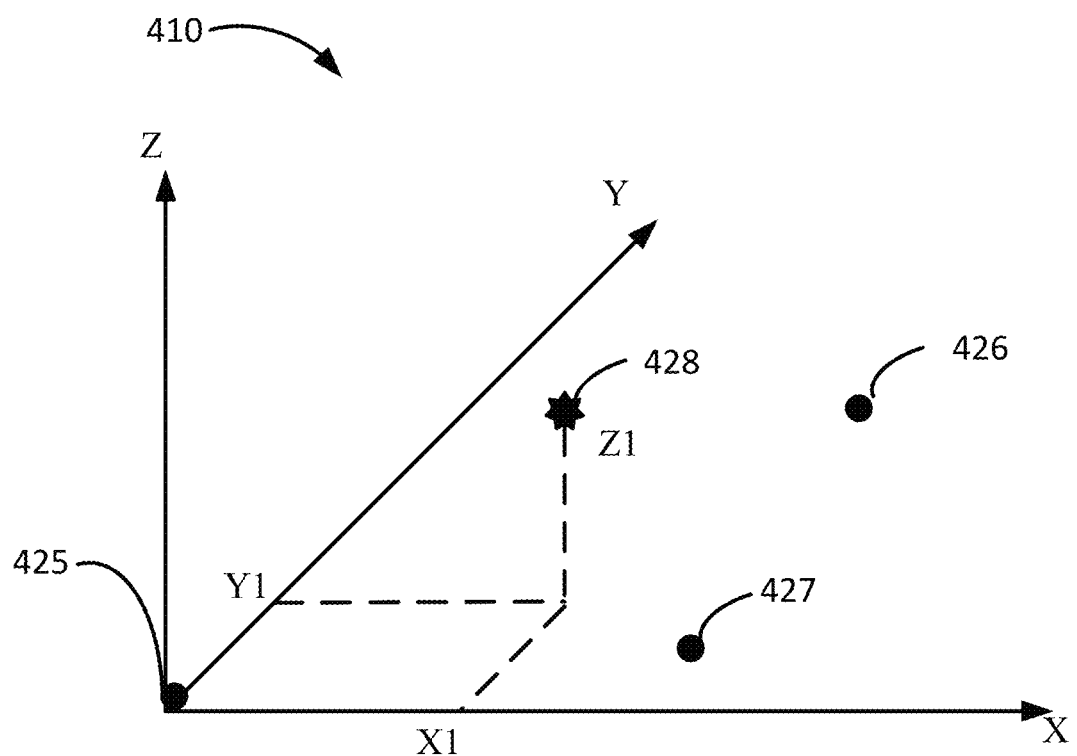
FIG. 4B schematically illustrates an embodiment of a Cartesian reference frame.

FIG. 4B schematically illustrates a Cartesian reference frame 410 that may be produced, for example, by the triangulation system described above. Points 425 and 426 represent the locations of the two triangulation reference transmitters 406 disposed respectively at diagonally related corners 119 of the building 110 in FIG. 4A, and point 427 represents the location of the triangulation reference transmitter 406 disposed at the front door 117 of the building 110. Those three points define the three-dimensional Cartesian reference frame 410.

The agent 99 carries a locator device (or positioning device) 90 having a transmitter 91, such as a radio transmitter. The array of triangulation receivers 405 receives a signal from the transmitter 91. Through the well-known geometrical process of triangulation, the location of the agent 99, within the 3D reference frame (X, Y, Z axes), can be determined with a degree of accuracy sufficient to render an avatar 299 of the agent 99 within a model of the building 110.

To that end, in preferred embodiments, a building model 310 may then be correlated to that reference frame, to provide a registration between the building 110 and the reference frame.

Other embodiments locate the agent 99 within the building 110 using GPS. In such embodiments, the locator device 90 may include a global positioning system ("GPS") receiver 93. As known in the art of GPS, the GPS receiver locates itself in a reference frame defined by a constellation of satellites in orbit around the Earth, to produce, as locator information, GPS coordinates of the agent.

Another illustrative embodiment determines the location of the agent 99 within the building 110 through the use of building infrastructure, also schematically illustrated in FIG. 4A. For example, the building 110 may include internal sensors 430 in known locations of the building 110. The internal sensors 430 are disposed at know locations in the building, and therefore define a reference frame. For example, the locations of the internal sensor 430 may be registered to a CAD model of the building 110. In such a case, when a given one of the internal sensors 430 detects the presence of an agent 99, the location of the agent 99 within the building 110 is known to be at the location of the internal sensor 430.

To that end, an agent 99 may carry a locator device 90 (which, in some embodiments, is in the form of a badge) that is detectable by the sensors 430 within the building 110. For example, a locator device 90 may carry a circuit that responds to queries from the sensors 430 built-in to the building. In other embodiments, the sensors 430 may be cameras, such as security cameras.

A preferred embodiment determines the location of the agent 99 within the building using magnetic sensing. It is known that a building 110, and more specifically the constituent materials of a building 110, distort the Earth's magnetic field (as used herein, "EMF" refers to "Earth's magnetic field") in detectable ways. The distortion varies throughout the building 110. For example, a steel column 115 that forms part of the building's structure may distort the Earth's magnetic field. When measuring the Earth's magnetic field within the building 110 with a magnetic sensor 92 (e.g., a magnetometer; such sensors are commonly found in some modern smart phones), the closer the magnetic sensor 92 is to the steel beam 115, the greater, or at least more distinctive, the distortion.

Figure 4C:
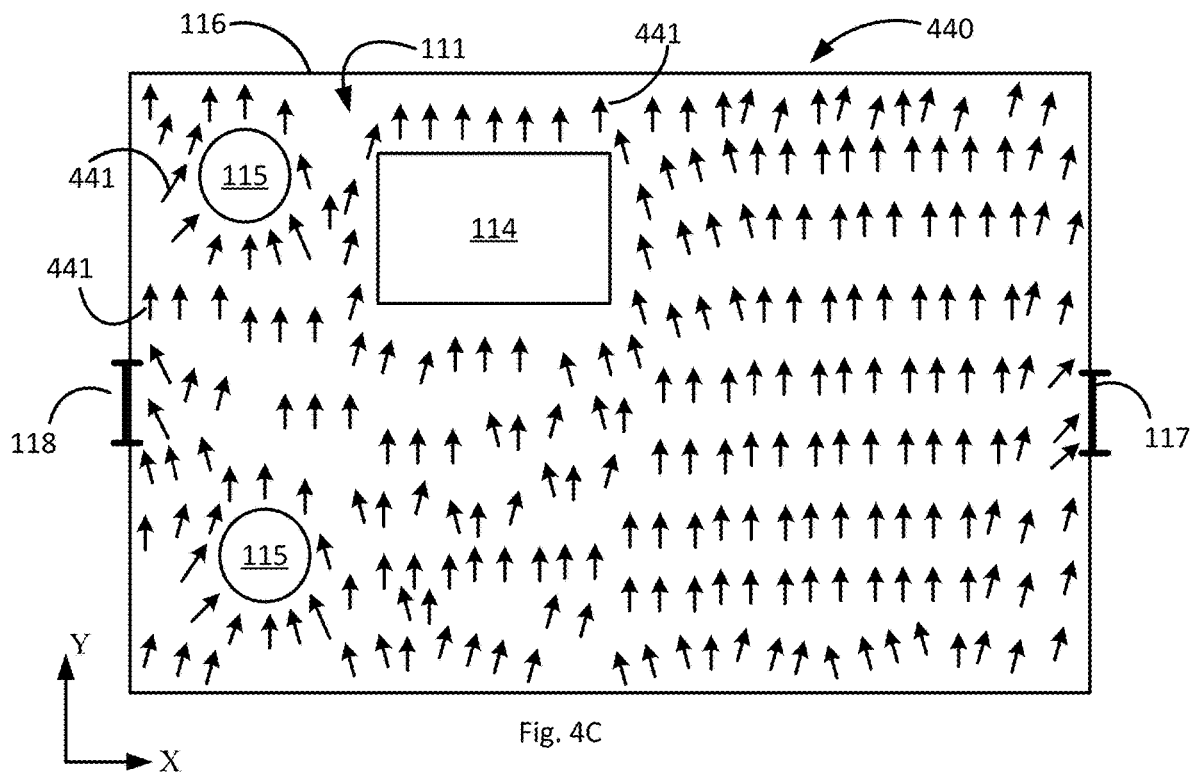
FIG. 4C schematically illustrates an embodiment of a magnetic map of the building.

As schematically illustrated in FIG. 4C, a plurality of magnetic readings taken throughout the building 110 form an array of magnetic vectors 441 that collectively be referred to as a "magnetic map" 440 (or "EMF map") of the building 110. The magnetic map 440 is an embodiment of a reference frame 400. Each magnetic reading is a measurement of the Earth's magnetic field at the point in space at which the reading was taken. Typically, such readings are taken by a person moving through open spaces in the building 110 (such as hallways, rooms, stairwells, etc.)

Figure 4D:
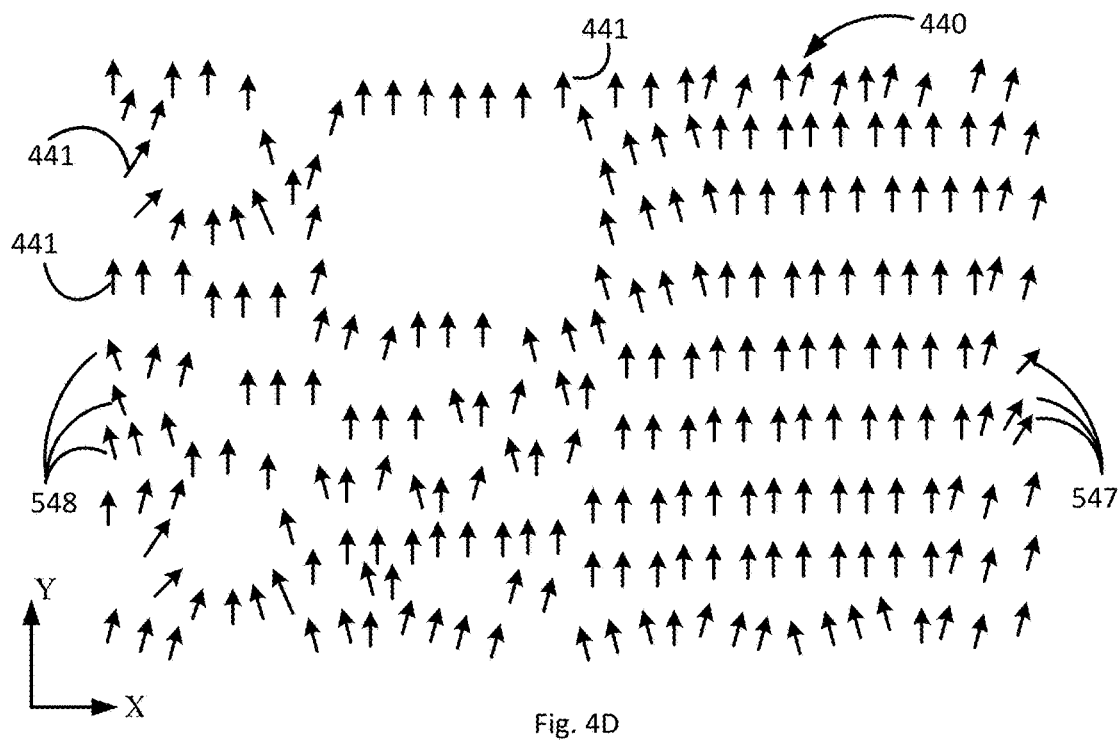
FIG. 4D schematically illustrates an embodiment of a magnetic map reference frame of the building.
Figure 5A:
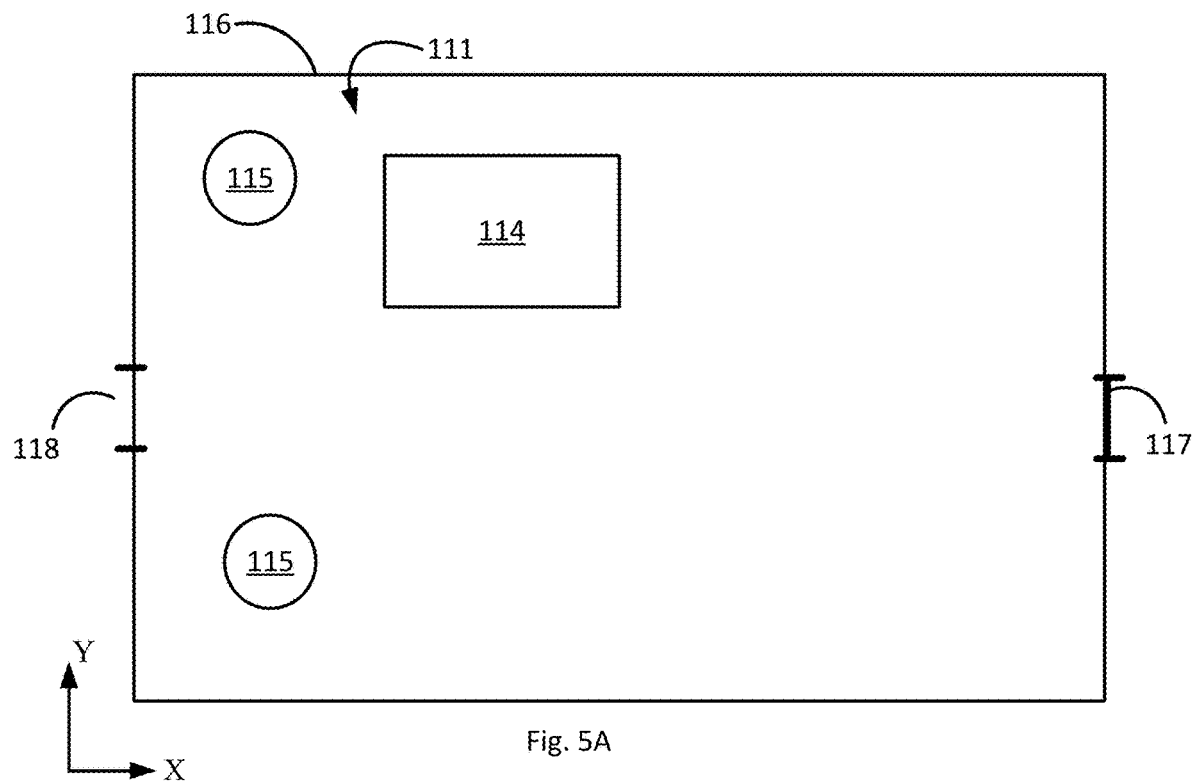
FIG. 5A and FIG. 5B schematically illustrate an embodiment of a correlation of a building model to a reference frame.
Figure 5B:
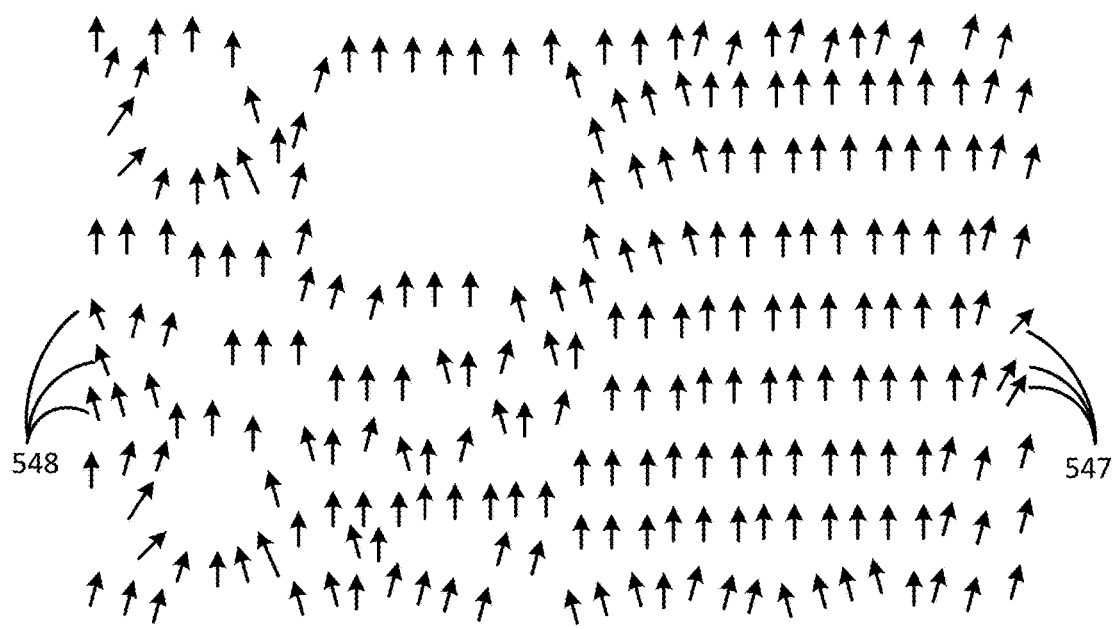

In FIG. 4C and FIG. 4D, each magnetic vector 441 is represented by an arrow. The orientation of the arrow (relative to the X-Y axis in those figures) graphically represents the direction of the Earth's magnetic field at that point, and the length of the arrow graphically represents the strength of the Earth's magnetic field at that point. It should be noted that, in preferred embodiments, each magnetic vector represents the EMF in three dimensions, for example orthogonal X, Y and Z axes.

It should be noted that such magnetic vectors 441 do not show or reveal physical features of the building 110. For example, from FIG. 4C it will be understood that the magnetic vectors 441 were taken around the first floor 111 of the building 110, but that no readings were taken from within the columns 115, or within the stairs 113. This is because the magnetic sensor that was used to create the magnetic map 440 cannot be placed within a solid object in order to take a reading there. FIG. 4D schematically illustrates the arrows with the context of the walls 116, columns 115, and stairs 113 of building 110 omitted. As shown, the magnetic vectors 441 do not show the walls 116, columns 115, and stairs 113 of building 110. It may be said that a magnetic map 440 only shows open spaces within a building 110. In other words, a magnetic map 440 shows where building features (e.g., stairways 113; columns 115; walls 116) are not.

Once a magnetic map 440 of a building 110 has been established, the location of an agent 99 within the building 110 may be determined by measuring the (distorted) Earth's magnetic field at a set of locations of the agent 99, and matching that set of measurements to a corresponding set of magnetic vectors 441 from known locations on the magnetic field map (i.e., from known locations within the building 110). As used herein, the term "set" means at least one. The match identifies the location of the agent 99 relative to the magnetic map.

To that end, the agent carries a magnetic sensor 92, such as magnetic sensors found in many modern cellular phones. Data representing each measurement from the set of measurements is transmitted to a system 700, as described below.

Consequently, some less-preferred embodiments supplement a magnetic map with a floorplan (e.g., a 2D representation of a portion of the building 110) or other 2D architect's drawing. Such 2D renderings are less desirable than, for example, a 3D CAD rendering or a 3D point cloud, as discussed above, because they fail to include details required to produce a 3D rendering of the interior of the building 110.

Correlating Location Information to Building Model

Once the location of the agent 99, within the building 110, is known [for example, relative to a reference frame 400 (e.g., a GPS reference frame; a Cartesian system 410 or magnetic map 440)], the location of the agent 99 can be correlated to a 3D building model 310 to produce a correlated location. More specifically, when the location of the agent 99 within the building 110 is correlated to a reference frame 400, and the reference frame is correlated to a building model 310, then the location of the agent 99 within the building model 310 is known.

An illustrative embodiment identifies at least one, and preferably two or three, locations in the 3D building model 310 that have known correlations to the location information that identifies the location of the agent 99.

In an illustrative embodiment, if the 3D model 310 is a point cloud of the interior of the building 110, it may include a front door 117 and a back door 118 of the building 110.

If the location of the agent 99 is known in GPS coordinates, and the GPS coordinates of locations of the building (e.g., GPS coordinates of the front door 117 and back door 118) are known, then the location of the agent 99 is known relative to the locations of the front door 117 and back door 118.

In other embodiments, a Cartesian reference frame 410 is defined by points 425, 426 and 427, and more specifically by the location of those points relative to triangulation receivers 405. The location of the agent 99 is also known, relative to triangulation receivers 405. Consequently, the location of the agent 99 can be correlated to the Cartesian reference frame 410, as schematically illustrates by point 428 in FIG. 4B.

Similarly, a magnetic map reference frame 440 may include magnetic readings for the front door 117 and back door 118. The location of the agent 99 within the magnetic map 440 is also known, and so the location of the agent 99 can be correlated to the magnetic map 440.

Next, the building model 310 may be correlated to the reference frame 400, and therefore to the location of the agent 99. In general, features of a building model 310 can be registered or aligned to a reference frame 400.

For example, by manipulating the points of a point cloud, the front door 317 and back door 318 of the point cloud (or, more specifically, the point cloud data representing the front door and back door) may be registered or aligned to the front door and back door of the reference frame 400. Similarly, the front door 317 and back door 318 of a CAD model may be registered or aligned to the front door and back door of the reference frame 400.

In these ways, the location of the agent 99 within the building is registered to the building model 310.

Rendering Composite Image

Figure 2A:
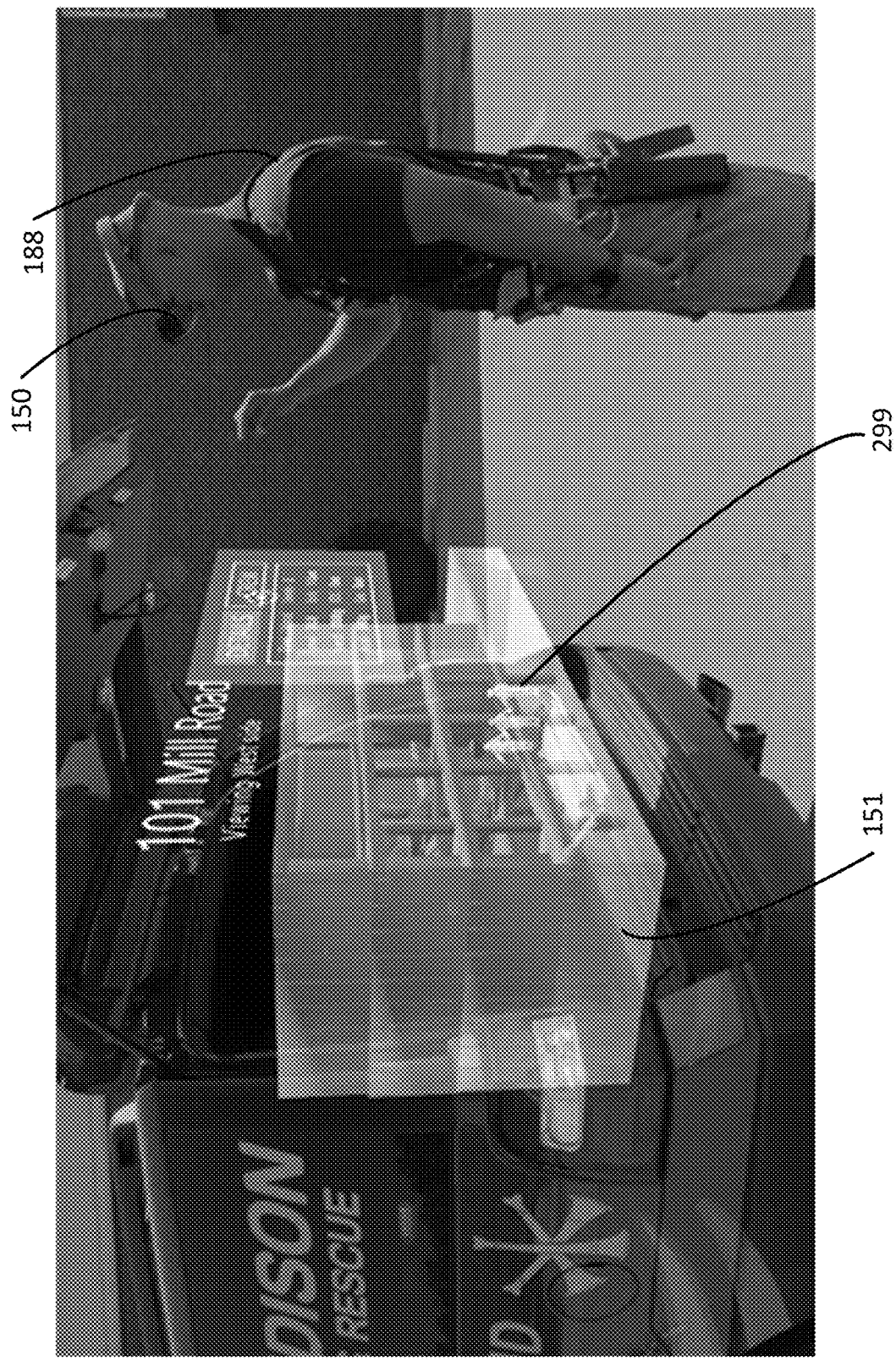
FIG. 2A schematically illustrates a user viewing a 3D virtual display showing locations of agents within a building.
Figures 2B, 2C:
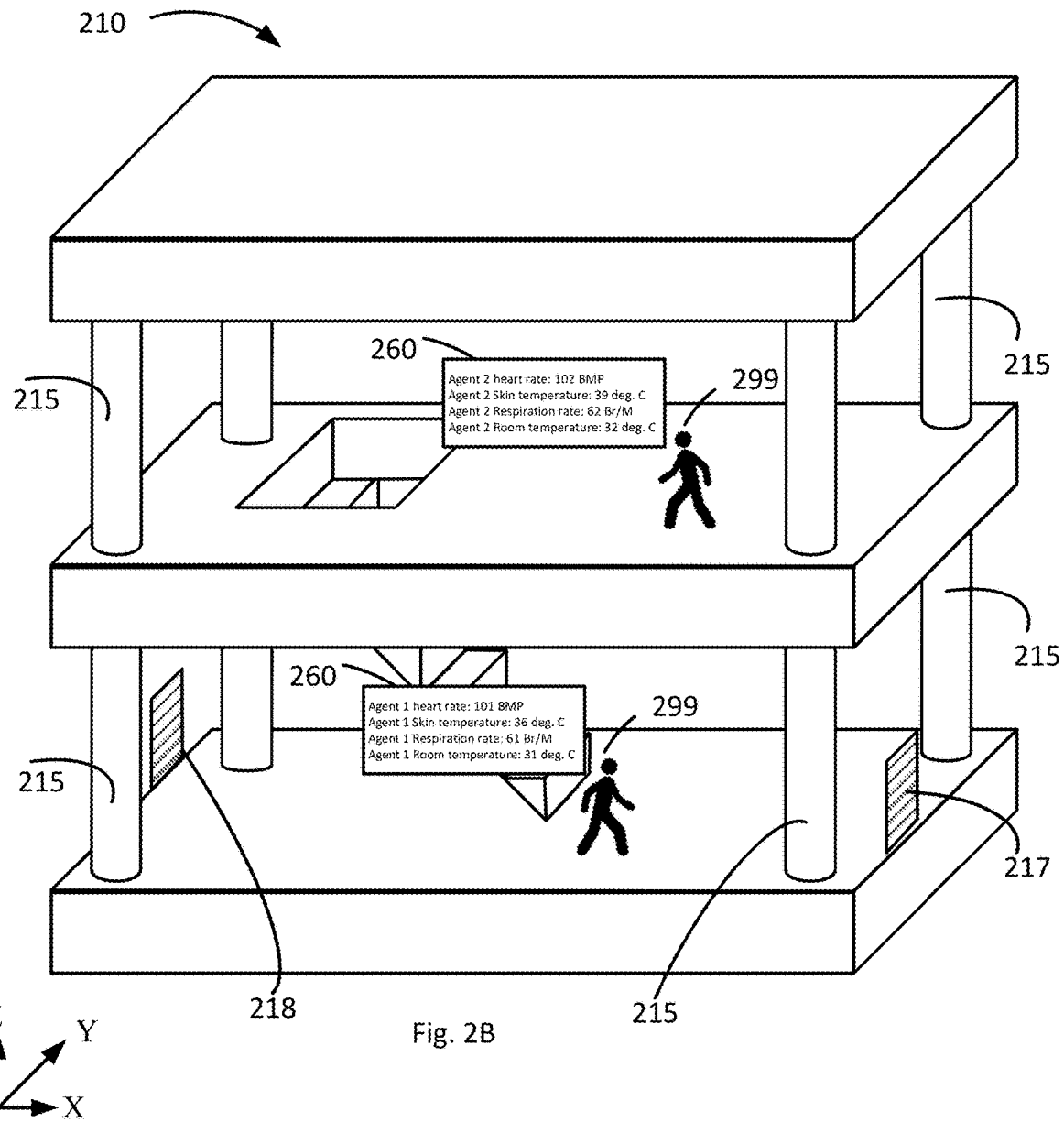
FIG. 2B and FIG. 2C schematically illustrate an embodiment of 3D virtual display of a building.

Once the location of the agent 99 is correlated to a 3D building model 310, a 3D rendering 210 of the building 110 may be generated and displayed on display device 150. Such a rendering includes an avatar 299 of the agent 99 displayed in the 3D rendering of the building in the location of the actual agent 99 within the actual building, and may be referred to as a "composite image." For example, as schematically illustrated by FIGS. 4A and 2B, if the agent 99 is walking across the second floor 112 of the building 110, the 3D rendering would show the avatar 299 at the same location on the second floor of the 3D rendering 210 of the building.

System

FIG. 7 schematically illustrates a system 700 for implementing embodiments described above. The system 700 includes modules interconnected by a communications bus 701.

Communications module 710 includes circuitry configured to communicate with other devices, such as location device 90 and databases 131, 132 (e.g., if those databases are not within database module 730) to name but a few examples. In some embodiments the communication module 710 may include receiver 120, although in other embodiments the receiver 120 is separate from, but in data communication with, communication module 710.

Some embodiments also include a model receiver 711, configured to procure a 3D model of the building 110. For example, a model receiver 711 may procure a 3D model of the building 110 from a capture device (e.g., mapping modality 800, described below) or a remote database 132, to name but a few examples.

Some embodiments also include a reference frame receiver 712 configured to procure reference frame (or "locator map") 410 for the building 110. For example, a model receiver 711 may procure a 3D model of the building 110 from a remote database, for example if the reference frame 410 is not available from database module 730. In keeping with the examples above, the reference frame 400 may be a magnetic map of the building 110, a GPS map of the building 110, or a Cartesian reference frame that coordinates places within the building to triangulated locations, to name but a few examples.

The system 700 also includes a correlation module 720. The correlation module 720 is configured to correlate the reference frame 400, the locator information of the agent 99, and the building model 310, as described above.

The rendering module 740 generates the 3D rendering 210 for display on the display device 150. As discussed above, the avatar 299 is displayed such that the displayed location of the avatar 299 is in the same position, relative to the 3D rendering, as is the agent 99 relative to the building 110. In other words, the avatar 299 accurately shows the location of the agent 99 within the building 110.

A user interface module 750 receives manipulator input provided by an observer 188 to manipulate the 3D rendering 210.

The display interface 760 interfaces with the display device 150 to cause the display device 150 to display the 3D rendering 210 to the observer 188. In preferred embodiments, the display interface 760 also receives manipulator input provided by the observer 188.

Contemporaneous Capture Modality

Figure 8:
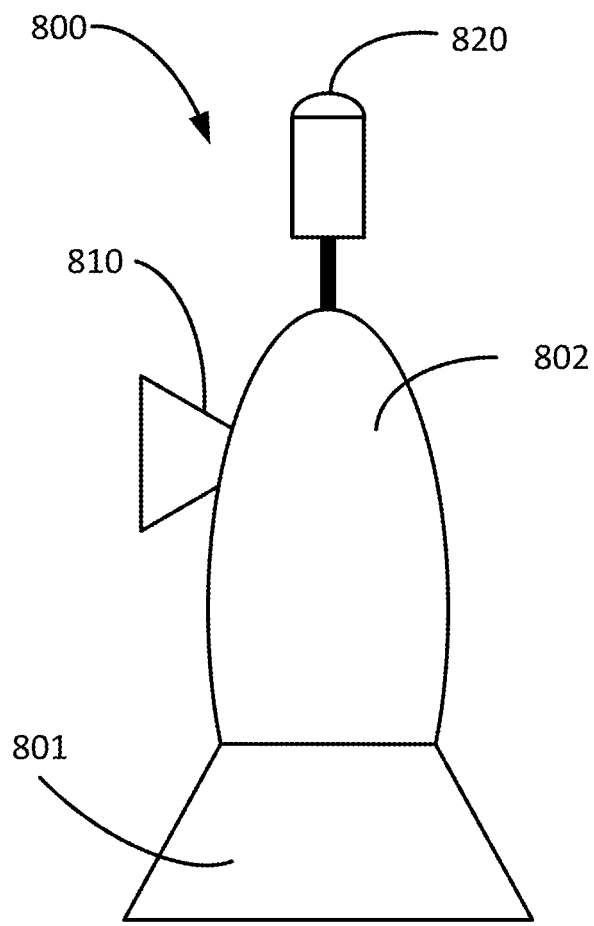
FIG. 8 schematically illustrates an embodiment of a contemporaneous capture modality.

FIG. 8 schematically illustrates a contemporaneous capture modality 800.

In illustrative embodiments, the modality 800 includes a magnetic sensor (e.g., magnetometer) 810 and a laser scanner 820 coupled to a chassis 802. In operation, the modality moves (or is moved) through the interior of the building 110, and takes measurements of the interior of the building as is goes. More specifically, in preferred embodiments the magnetic sensor 810 takes magnetic readings 440 (as described above) of the building 110 and the laser scanner 820 takes physical measurements of the interior of the building 110 to produce a point cloud.

In preferred embodiments, the magnetic sensor 810 and laser scanner 820 take their respective readings and measurements contemporaneously, with the result that the readings and measurements are correlated to one another, in what may be referred to as a "composite model." Use of a composite model has the benefit of eliminating the need (and process step) to correlate a separate reference frame 400 and building model 310.

To that end, in preferred embodiments, the magnetic sensor 810 and laser scanner 820 are coupled to the chassis 802 in a fixed physical and spatial relationship to one another.

In some embodiments, the modality 800 is carried, by a worker, through the building in order to take the readings and measurements. For example, the modality 800 may be carried by hand, in a backpack, or wheeled through the building 110 on a cart.

In preferred embodiments, the modality 800 includes a conveyor 801. The conveyor 801 is an autonomous vehicle configured to, and capable of, navigating and moving throughout open spaces, such as rooms, hallways, etc., in the building 110. For example, the conveyor 801 may include a motor, wheels and navigation circuitry known for such purposes, such as those in various vacuum appliances available from the iRobot Corporation™.

The modality 800 stores the readings and measurements in one or more databases (e.g., either or both of database 131 and database 132). In preferred embodiments, the modality stores the readings and measurements as a composite model described above, but in some embodiments may store the readings and measurements separately in database 131 and database 132, respectively.

REFERENCE NUMBERS

Reference numbers used herein include the following:
- 90: Locator device;
- 91: Radio transmitter;
- 92: Sensor;
- 93: GPS receiver;
- 99: Agent;
- 100: System;
- 110: Building;
- 111: First floor of building;
- 112: Second floor of building;
- 113: Stairs in building;
- 114: Stairwell;
- 115: Column;
- 116: Wall of building;
- 117: Front door;
- 118: Back door;
- 120: Receiver;
- 121: Antenna;
- 131: Building reference frame database;
- 132: Building physical model database;
- 150: Display device;
- 151: 3D image;
- 170: Remote terminal;
- 188: Manager;
- 210: 3D rendering of building;
- 213: Rendered stairway;
- 215: Rendered column;
- 217: Rendered front door;
- 218: Rendered back door;
- 260: Biometric display;
- 261: Biometric data;
- 299: Avatar;
- 310: Building model;
- 311: Example rendered model;
- 330: Point cloud of building;
- 331: Point cloud of first floor;
- 332: Point cloud of second floor;
- 333: Point cloud of stairs;
- 335: Pont cloud of column;
- 350: CAD model of building;
- 351: CAD model of first floor of building;
- 352: CAD model of second floor of building;
- 353: CAD model of stairs in building;
- 354: CAD model of stairwell;
- 355: CAD model of column;
- 400: Reference frame;
- 405: Triangulation receiver;
- 406: Triangulation reference transmitter;
- 410: Cartesian reference frame;
- 425: First corner point;
- 427: Second corner point;
- 427: Front door point;
- 428: Location of agent;
- 430: Inside sensor;
- 440: Magnetic map;
- 441: Magnetic vector;
- 547: Front door registration magnetic vector;
- 548: Back door registration magnetic vector;
- 800: Mapping modality;
- 801: Conveyor;
- 802: Chassis;
- 810: Magnetic sensor;
- 820: Point cloud scanner.

Embodiments summarized above and described in further detail below have the effect of transforming the nature of interaction between a person inside of a building and an observer of that person's location within the building from one that has existed in the physical world, typically based on personal observation (e.g., the observer looking through a window or watching via security camera), to one that includes the cyberspace activity of remotely locating the person within the building and generating a virtual display of an avatar of the person with a 3D rendered image of the building. In general, illustrative embodiments are enabled by the technology infrastructure that is claimed and described herein. For these reasons, among others, the activities defined by the claims below are not well-understood, routine, or conventional to a skilled artisan in the field of the present invention.

Various embodiments of the invention may be implemented at least in part in any conventional computer programming language. For example, some embodiments may be implemented in a procedural programming language (e.g., "C"), or in an object-oriented programming language (e.g., "C++"). Other embodiments of the invention may be implemented as preprogrammed hardware elements (e.g., application specific integrated circuits, FPGAs, and digital signal processors), or other related components.

In an alternative embodiment, the disclosed apparatus and methods may be implemented as a computer program product for use with a computer system. Such implementation may include a series of computer instructions fixed on a tangible medium, such as a non-transient computer readable medium (e.g., a diskette, CD-ROM, ROM, FLASH memory, or fixed disk). The series of computer instructions can embody all or part of the functionality previously described herein with respect to the system.

Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies.

Among other ways, such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A system for identifying the location of an agent within an interior of a building, the system comprising:
   a set of triangulation reference receivers disposed outside of the building, the set of triangulation reference receivers disposed to receive locator information from a transmitter with the agent;
   a model receiver configured to procure a 3D model of the interior of the building;
   a correlator configured to correlate the 3D model to a reference frame, and to correlate the location of the agent to the reference frame, to produce a correlated location representing the location of the agent within the building;
   a rendering module configured to render a 3D image from the 3D model and correlated location, the 3D image including an avatar representing the agent at the correlated location within the 3D image; and
   a 3D display device in communication with the rendering module, the 3D display device configured to receive and display, to a user, the 3D image.

2. The system of claim 1 further comprising a set of reference transmitters disposed around the building, the reference transmitters defining the reference frame.

3. The system of claim 1 further comprising a telemetry receiver configured to receive, from a transmitter with the agent, telemetry data, wherein the correlator is further configured to correlate the telemetry data with the correlated location.

4. The system of claim 3, wherein the telemetry data is biotelemetry data comprising at least one of:
   skin temperature of the agent;
   respiration rate of the agent; and
   heart rate of the agent.

5. The system of claim 3, wherein the rendering module is further configured to render, into the 3D image, a telemetry window at the correlated location so that the telemetry data is visually associated with the agent represented by the avatar.

6. The system of claim 1, wherein the correlator is further configured to:
   correlate the locator information to the reference frame, and to
   correlate the reference frame to the building model.

7. The system of claim 1, further comprising a locator device disposed with the agent in the building, the locator device comprising a transmitter configured to transmit the locator information.

8. The system of claim 7, wherein the locator device further comprises a magnetic sensor in data communication with the transmitter.

9. A non-transitory computer-readable medium containing computer-executable code which, when executed by a computer processor, causes the computer processor to perform a method of displaying a location of an agent within a building, the computer-executable code comprising computer code for:
   receiving locator information from the agent, the locator information indicating the location of the agent relative to a reference frame;
   receiving a 3D model of the interior of the building;
   correlating the 3D model to the reference frame, to produce a correlated location representing the location of the agent within the building;
   rendering a 3D image from the 3D model and correlated location, the 3D image including an avatar representing the agent at the correlated location within the 3D image; and
   displaying, on a 3D display device, the 3D image.

10. The non-transitory computer-readable medium of claim 9, wherein the computer-executable code further comprises computer code for:
    receiving, from a transmitter with the agent, telemetry data; and
    correlating the telemetry data with the correlated location; and
    rendering into the 3D image a telemetry window at the correlated location so that the telemetry window is visually associated with the agent represented by the avatar.

11. The non-transitory computer-readable medium of claim 10, wherein the computer-executable code for rendering into the 3D image a telemetry window at the correlated location further comprises computer code for:
    rendering into the 3D image a telemetry window at the correlated location in response to user input received at the displayed avatar.

12. The non-transitory computer-readable medium of claim 9, wherein the computer-executable code for correlating the 3D model to the reference frame further comprises computer code for:
    procuring a reference frame; and
    correlating both the locator information and the building model to the reference frame.

13. The non-transitory computer-readable medium of claim 12, wherein
    the locator information comprises a set of magnetic readings from the location of the agent within the building;
    the reference frame comprises a plurality of magnetic vectors from known locations within the building; and
    the computer code for correlating both the locator information and the building model to the reference frame comprises computer code determining the correlated location of the agent within the building by matching the set of magnetic readings to a corresponding set of magnetic vectors.

14. The non-transitory computer-readable medium of claim 9, wherein the 3D model comprises a point cloud, and the computer code for correlating the 3D model to the reference frame comprises computer code for correlating the point cloud to the reference frame.

15. A system for identifying the location of an agent within an interior of a building, the system comprising:
    means for receiving locator information from the agent, the locator information indicating the location of the agent relative to a reference frame;
    means for procuring a 3D model of the interior of the building;
    means for correlating the 3D model to the reference frame, to produce a correlated location representing the location of the agent within the building;
    means for rendering a 3D image from the 3D model and correlated location, the 3D image including an avatar representing the agent at the correlated location within the 3D image; and
    means for receiving, and displaying to a user, the 3D image, said means in communication with the rendering module.

16. The system of claim 15 further comprising means for receiving, from a transmitter with the agent, telemetry data, wherein the means for correlating is further configured to correlate the biotelemetry data with the correlated location.

17. The system of claim 16, wherein the telemetry data comprises the room temperature of the agent's location within the interior of the building.

18. The system of claim 16, wherein the telemetry data is biotelemetry data comprising at least one of:
 skin temperature of the agent;
 respiration rate of the agent; and
 heart rate of the agent,
 and the means for receiving telemetry date comprises a means for receiving at least one of said biotelemetry data.

19. The system of claim 16, wherein the means for rendering is further configured to render, into the 3D image, a telemetry window at the correlated location so that the telemetry data is visually associated with the agent represented by the avatar.

20. The system of claim 15, further comprising:
 means for procuring a reference frame; and
 wherein the means for correlating is further configured to:
  correlate the locator information to the reference frame, and to
  correlate the reference frame to the building model.

21. The system of claim 15, further comprising a locator device disposed with the agent in the building, the locator device comprising a transmitter configured to transmit the locator information.

22. The system of claim 21, wherein the locator device further comprises a magnetic sensor in data communication with the transmitter.

23. A system for identifying the location of an agent within an interior of a building, the system comprising:
 a set of sensors disposed at locations throughout the building, the locations defining a reference frame relative to the building;
 a location receiver configured to obtain locator information from the agent, the locator information indicating the location of the agent relative to the sensors;
 a correlator configured to correlate a 3D model of the interior of the building to the reference frame, and to correlate the location of the agent to the reference frame to produce a correlated location representing the location of the agent within the building;
 a rendering module configured to render a 3D image from the 3D model and correlated location, the 3D image including an avatar representing the agent at the correlated location within the 3D image; and
 a 3D display device in communication with the rendering module, the 3D display device configured to receive and display, to a user, the 3D image.

24. The system of claim 23, further comprising:
 a model receiver configured to procure the 3D model of the interior of the building.

25. The system of claim 23 further comprising a telemetry receiver configured to receive, from a transmitter with the agent, telemetry data, wherein the correlator is further configured to correlate the telemetry data with the correlated location.

26. The system of claim 25, wherein the telemetry data comprises the room temperature of the agent's location within the interior of the building.

27. The system of claim 25, wherein the telemetry data is biotelemetry data comprising at least one of:
 skin temperature of the agent;
 respiration rate of the agent; and
 heart rate of the agent.

28. The system of claim 25, wherein the rendering module is further configured to render, into the 3D image, a telemetry window at the correlated location so that the telemetry data is visually associated with the agent represented by the avatar.

29. The system of claim 23, wherein the correlator is further configured to:
 correlate the locator information to the reference frame, and to correlate the reference frame to the 3D model of the interior of the building.

30. The system of claim 23, further comprising a locator device disposed with the agent in the building, the locator device comprising a transmitter configured to transmit the locator information.

31. The system of claim 30, wherein the locator device further comprises a magnetic sensor in data communication with the transmitter.

\* \* \* \* \*

UNITED STATES PATENT AND TRADEMARK OFFICE
CERTIFICATE OF CORRECTION

| | |
|---|---|
| PATENT NO. | : 11,635,519 B2 |
| APPLICATION NO. | : 16/846093 |
| DATED | : April 25, 2023 |
| INVENTOR(S) | : Andrew James England et al. |

It is certified that error appears in the above-identified patent and that said Letters Patent is hereby corrected as shown below:

In the Claims

At Column 15, Claim number 18, Line number 11, please replace "date" with --data--

Signed and Sealed this
Twenty-fifth Day of July, 2023

Katherine Kelly Vidal
*Director of the United States Patent and Trademark Office*